United States Patent [19]

Secretarski et al.

[11] Patent Number: 5,009,848
[45] Date of Patent: Apr. 23, 1991

[54] ON BOARD AUTOMATIC DIESEL ENGINE COOLING WATER CHEMICAL TREATMENT DISPENSING SYSTEM

[76] Inventors: James M. Secretarski, 6910 Dorn Rd., Hartland, Wis. 53029; Terry M. Crowell, W320 S8409 Bevllah Rd., Mukwonago, Wis. 53149

[21] Appl. No.: 189,373

[22] Filed: May 2, 1988

[51] Int. Cl.$^5$ ............................................. G01N 27/06
[52] U.S. Cl. ..................................... 422/62; 422/110; 422/117; 422/119; 422/261; 422/274; 422/283; 123/41.01; 137/268; 137/551
[58] Field of Search .......... 422/62, 110, 113, 117–119, 422/108, 261, 274, 283; 137/268, 551; 215/2; 220/400; 222/52; 123/41.01

[56] References Cited

U.S. PATENT DOCUMENTS

| | | |
|---|---|---|
| 1,242,905 | 10/1917 | Atkinson ............................. 422/274 |
| 1,934,304 | 11/1933 | Guth .................................... 422/274 |
| 2,677,601 | 5/1954 | Ruth .................................... 422/113 |
| 3,864,090 | 2/1975 | Richards ............................. 422/274 |
| 3,918,469 | 11/1975 | Zamboni et al. |
| 4,464,315 | 8/1984 | O'Leary. |
| 4,659,459 | 4/1987 | O'Leary et al. |
| 4,892,707 | 1/1990 | Stockton et al. ..................... 422/113 |

Primary Examiner—Robert J. Warden
Assistant Examiner—Timothy M. McMahon
Attorney, Agent, or Firm—Andrus, Sceales, Starke & Sawall

[57] ABSTRACT

A water treatment dispensing apparatus for an engine cooling system, such as in a diesel locomotive, includes one or more probes for measuring the conductivity of the fluid circulating in the system. From the conductivity of the fluid, a determination of the level of concentration of treatment chemicals in the fluid can be ascertained. A comparator is utilized for determining whether, based on the conductivity readings of the fluid, the level of concentration of treatment chemicals in the fluid is at or above a desired level. When it is determined that the level of concentration has fallen below the desired level, a valve is actuated so as to divert a portion of fluid from the system to a chemical treatment dispensing apparatus. Simultaneously, an outlet valve is actuated to allow mixed fluid and chemical treatment to be routed back into the circulating system. The dispensing apparatus includes a housing adapted to receive a container for containing a quantity of chemical treatment therein. When fluid from the circulating system is diverted to the dispensing apparatus, the fluid flows through the housing and mixes with chemical from the canister. The mixed fluid and chemical treatment is then returned to the fluid circulating system through an outlet. A novel design for the dispensing canister is employed, as is a unique system for providing power to the dispensing apparatus from the electrical system of the locomotive.

13 Claims, 7 Drawing Sheets

ON BOARD AUTOMATIC DIESEL ENGINE COOLING WATER CHEMICAL TREATMENT DISPENSING SYSTEM

BACKGROUND AND SUMMARY

This invention relates to a system for treating water in a closed circulating system, and more particularly to a dispensing system for adding chemical treatment to a cooling water system for a diesel locomotive.

In a railroad locomotive, it is common to use water as an engine coolant due to well-known difficulties resulting from the use of glycol coolants or the like. In a locomotive cooling system, it is often difficult to prevent the loss of coolant water resulting from leaks or cracks within the system. As a result, it is often necessary to replenish the supply of water in the system to ensure that an adequate quantity of water is available for cooling the engine.

In a cooling system utilizing water as the coolant, it is desirable to maintain a certain level of concentration of chemical water treatment within the system to inhibit corrosion and buildup of scale within the system, as well as for other purposes. Because of the above-noted problems in maintaining an adequate quantity of water within the system, the level of concentration of the chemical treatment in the cooling water often falls below the optimal level.

Additionally, because of the nature of such a water cooling systems, when the locomotive is at rest and the ambient temperature is sufficiently low to create the potential for freezing of the water in the system, the water is dumped so as to empty the system and prevent damage which may be caused by such freezing. The cooling system is then refilled when it is desired to operate the locomotive, and it is often the case that the addition of proper chemical treatment to the water is neglected prior to operation.

As can be seen from the above, there is a need for a system which will automatically maintain a predetermined level of concentration of chemical treatment within the cooling water system. The present invention is designed to provide such an automatic system.

In accordance with the invention, an apparatus for maintaining a predetermined level of concentration of treatment chemicals or the like in a closed fluid circulating system includes a sensing means for monitoring the level of concentration of chemicals in the fluid circulating within the system. A chemical concentrate dispensing means is interconnected with the fluid circulating system. Flow control means responsive to the sensing means prevents the flow of fluid through the dispensing means when the level of concentration of chemicals in the fluid is at or above the predetermined level. When the level of concentration of treatment chemicals in the fluid falls below the predetermined level, the flow control means allows fluid from the fluid circulating system to circulate through the dispensing means and back into the fluid circulating system. In this manner, the level of concentration of chemicals in the fluid within the system is raised to the predetermined level. When the sensing means has determined that the level of concentration of the chemicals in the fluid is at or above the predetermined level, the flow control means discontinues circulation of fluid through the dispensing means.

In one embodiment, the sensing means comprises a probe for measuring the conductivity of fluid within the fluid circulating system, and thereby the level of concentration of chemicals in the fluid. A comparator is utilized for ascertaining whether, based on the conductivity reading of the fluid, the level of concentration is satisfactory. The dispensing means comprises a fluid inlet connected to the fluid circulating system for routing at least a portion of fluid from the system. A housing having an interior cavity in fluid communication with the inlet is adapted to receive fluid therefrom. A replaceable dispensing canister adapted to hold a quantity of soluble chemical treatment is disposed within the interior cavity of the housing. A passage is provided for allowing fluid to pass from the interior of the housing into the canister for mixing the fluid with the soluble chemical treatment. A passage is also provided for allowing the mixed fluid and chemical treatment to pass from the canister to a fluid outlet connected between the fluid circulating system and the passage, for routing the mixed fluid and chemical treatment back into the circulating system.

A novel design is employed for the canister located within the housing of the dispensing means. The canister is provided with a bottom wall and an upstanding side wall extending therefrom to define a canister interior having a transverse dimension less than that of the interior cavity of the housing. A fluid flow path is thus formed between the side wall of the housing and the side wall of the canister. Passage means is disposed between the fluid flow path and the interior of the canister to allow fluid to pass into the canister interior for mixing the fluid with the chemical treatment. Discharge means is in fluid communication with the canister interior for discharging mixed fluid and chemical treatment therefrom. In one embodiment, the passage means comprises a series of openings formed in the bottom wall of the canister. The fluid flows downwardly through the flow path between the canister side wall and the housing side wall to the bottom of the canister, and then upwardly through the openings and into the interior of the canister to mix with the concentrated chemical treatment contained therein. In one embodiment, the discharge means comprises a dip tube extending downwardly into the interior of the canister, and having an opening for receiving mixed fluid and chemical treatment therefrom.

The invention also incorporates a mechanism for relieving pressure within the housing of the dispensing apparatus prior to gaining access to the housing interior for replacing the canister. A line connects the housing interior to a dump valve open to ambient pressure. A switch, placed adjacent the housing, is operable to actuate the dump valve. Actuation of the dump valve relieves pressure in the housing interior prior to gaining access thereto, thereby providing a safety mechanism to prevent operator injury. The dip tube extending downwardly into the housing interior siphons a substantial quantity of liquid from the housing interior upon actuation of the dump valve, thereby providing a further mechanism for preventing operator injury. A secondary mechanism is employed for ensuring that pressure within the housing interior is relieved in the event the operator neglects to actuate the dump valve by means of the switch. A cover is mounted to the dispensing apparatus adjacent the housing and, when in a first position, prevents the operator from gaining access to the housing interior. The cover is movable to a second position for allowing access to the housing interior. A secondary switch, interconnected with the dump valve, is actuated when the cover is moved from the first position to the second position. This mechanism ensures that pressure in the housing interior is relieved prior to gaining access thereto for replacing the canister.

BRIEF DESCRIPTION OF THE DRAWINGS

The drawings illustrate the best mode presently contemplated of carrying out the invention.

In the drawings.

DETAILED DESCRIPTION OF THE PREFERRED EMBODIMENT

Figure 1:
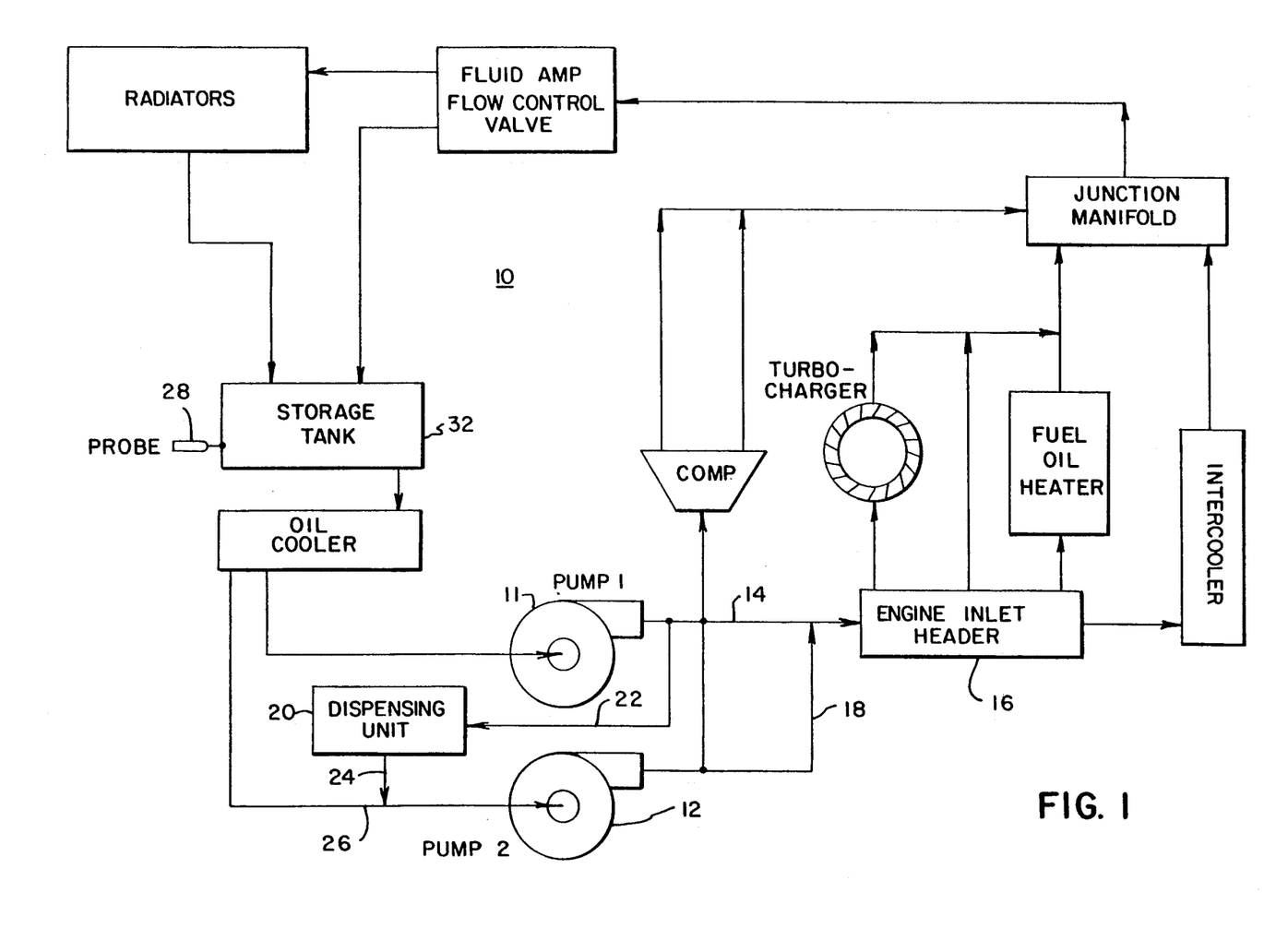
FIG. 1 is a schematic showing of a locomotive cooling system including the chemical treatment dispensing apparatus of the invention.

FIG. 1 illustrates a representative cooling system 10 for a diesel railroad locomotive. The schematic showing of the locomotive cooling system is believed to be self-explanatory, and only portions of the system relevant to the invention will be explained. Cooling system 10 includes a pair of pumps 11, 12 for pumping water therethrough. A line 14 connects pump 11 to an engine inlet header 16, and a line 18 connects pump 12 to header 16.

The treatment chemical dispensing apparatus of the invention is illustrated generally at 20. An inlet line 22 is interconnected between line 14 and dispensing apparatus 20 for directing a portion of cooling water from cooling system 10. An outlet line 24 is interconnected between dispensing apparatus 20 and a feed line 26 which supplies water to pump 12. Outlet line 24 routes mixed water and chemical treatment from dispensing apparatus 20 back into cooling system 10.

Dispensing apparatus 20 includes a probe 28 disposed in a water storage tank 32. Probe 28 senses the conductivity of water in cooling system 10, and may be a bayonet probe such as that manufactured by Knight Equipment under its designation BP-100. As will subsequently be explained, a determination of the level of concentration of chemical treatment in the cooling water can be made based on the conductivity of the water in system 10. Dispensing apparatus 20 is actuated when the level of concentration of chemical treatment within the system falls below a certain predetermined level. Water is then routed from cooling system 10 through inlet line 22 and into dispensing unit 20 for mixing with concentrated chemical treatment contained therein. After mixing, the mixed water and chemical treatment is routed through line 24 and back into cooling system 10 at feed line 26.

Figure 2:
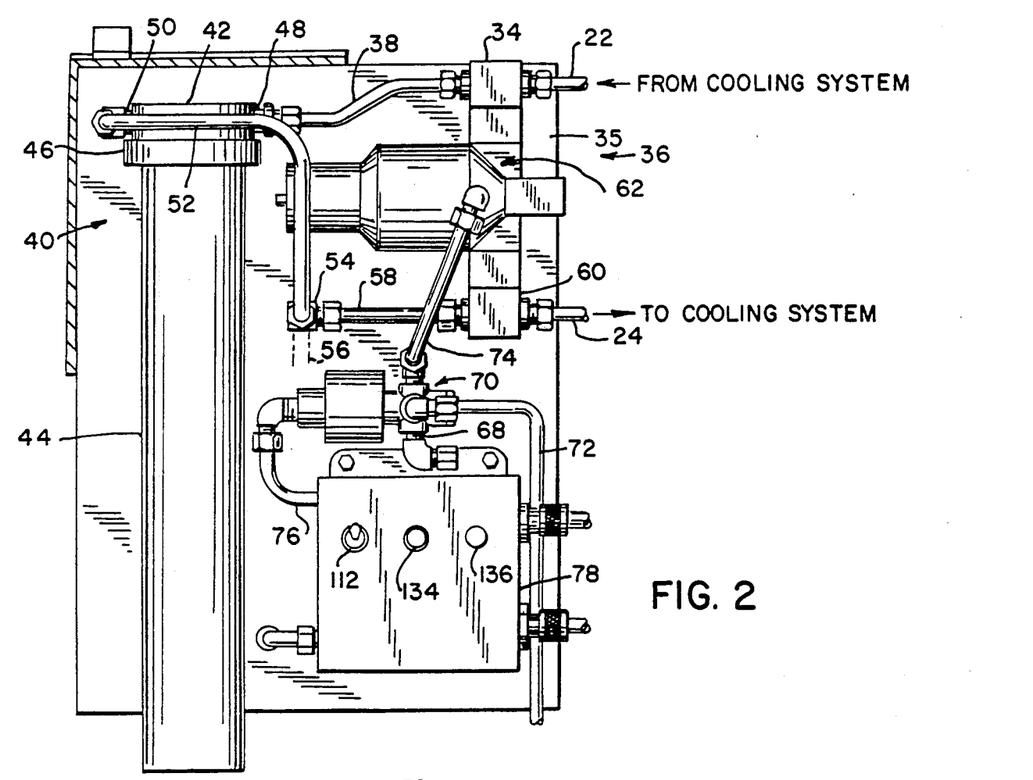
FIG. 2 is a front elevation view of the dispensing apparatus of the invention.
Figure 3:
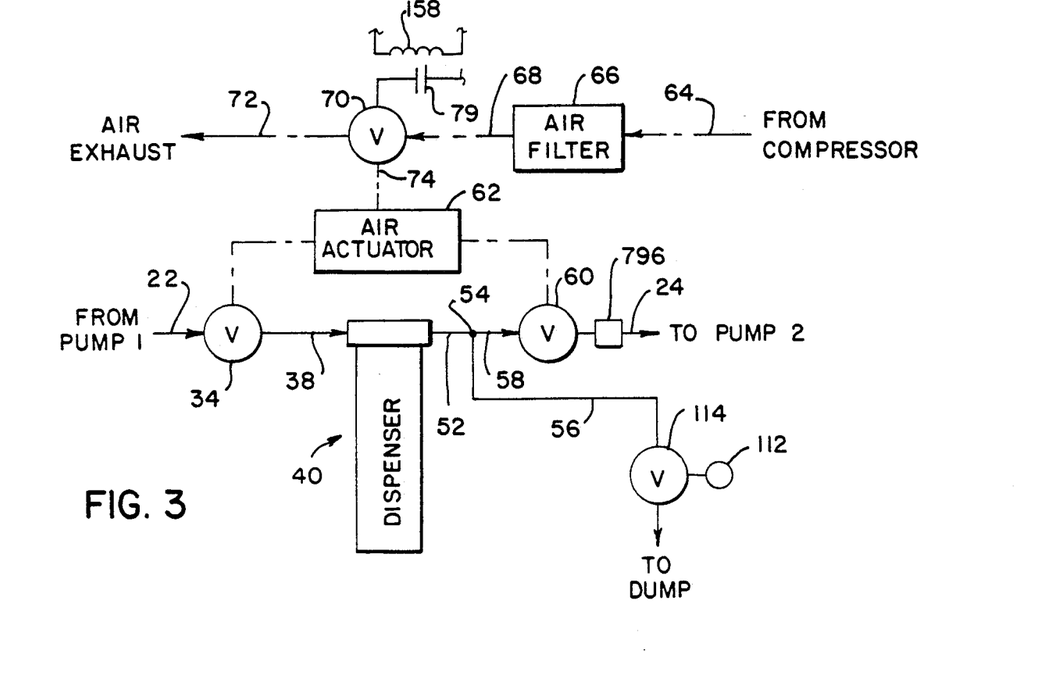
FIG. 3 is a schematic representation of the dispensing apparatus of FIG. 2.

FIG. 2 illustrates the physical arrangement of the various components of dispensing apparatus 20, and FIG. 3 schematically represents the relationship between such components. Inlet line 22 is connected to an inlet valve 34 mounted on a front plate 35 of a panel 36. A feed line 38 is connected between inlet valve 34 and a dispenser housing, shown generally at 40. Housing 40 includes a stationary upper portion 42 and a removable lower portion 44. A rotatable ring 46 is operable to engage the upper end of lower portion 44 for affixing lower portion 44 to upper portion 42. Ring 46 is also operable to allow lower portion 44 to be removed from upper portion 42, for reasons to be explained.

Upper portion 42 of dispenser housing 40 includes an inlet 48, to which feed line 38 is connected, and an outlet 50. A discharge line 52 is connected at one end to outlet 50 and at the other end to a tee 54. A dump line 56 is connected to tee 54, as is a line 58 extending between the stem of tee 54 and an outlet valve 60. Outlet line 24, which is connected at one end to feed line 26 for pump 12, is connected at its other end to outlet valve 60.

The disposition of inlet valve 34 and outlet valve 60 is controlled by an air actuator 62, also mounted to front plate 35 of panel 36. Compressed air is supplied to actuator 62 from an air compressor (not shown) via a compressor line 64 (FIG. 3). Compressor line 64 is connected to an air filter 66, from which an air supply line 68 extends. Supply line 68 is connected to an air solenoid valve 70, to which an exhaust 72 and a discharge line 74 are connected. Discharge line 74 is interconnected between air solenoid valve 70 and air actuator 62.

Air solenoid valve 70 is electrically connected via a conduit 76 to a conductivity control circuit contained within a box 78. As will subsequently be explained, when the conductivity readings of fluid within cooling system 10 fall below a certain predetermined level, a control relay 79 (FIG. 3) associated with the conductivity control circuit acts to energize the coil in air solenoid valve 70 so as to allow compressed air from line 68 to pass through valve 70 and line 74 into air actuator 62. The supply of compressed air to actuator 62 moves inlet valve 34 and outlet valve 60 to their open positions, so as to allow fluid flow therethrough. In this circumstance, fluid from cooling system 10 is routed from the discharge side of pump 11 through inlet line 22, through dispensing apparatus 20, and back to feed line 26 through outlet line 24.

As shown in FIG. 3, a variable pressure constant flow control valve, shown at 79b, is disposed in line 24. Valve 24 may be that such as manufactured by Dole Valve Corporation. Valve 24 ensures a constant flow of treated coolant despite varying pressure caused by fluctuating engine rpms.

Figure 4:
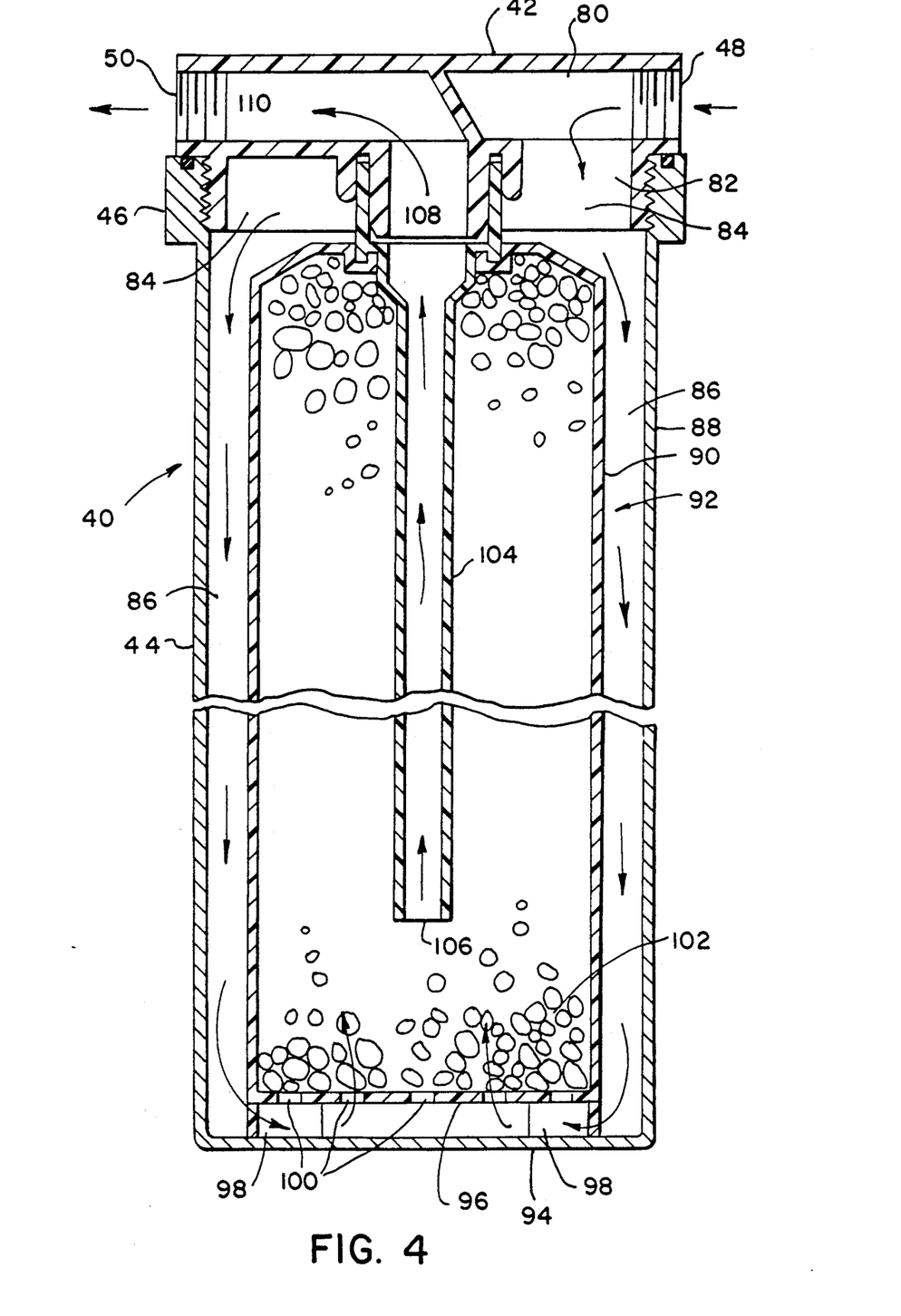
FIG. 4 is a cross sectional view showing the chemical concentrate dispensing housing of the dispensing apparatus of FIG. 2, including a canister for containing a quantity of chemical treatment.

FIG. 4 illustrates the internal construction of dispenser housing 40 and the manner in which cooling water is mixed with chemical treatment as it passes therethrough. As previously noted, water enters housing 40 through inlet opening 48. The water then flows into a cavity 80 formed in upper portion 42 of housing 40, and downwardly through a passage 82 and into an annular area 84 disposed in the lower end of upper portion 42. From annular passage 84, water flows downwardly through a water flow path 86. Flow path 86 is defined by an upstanding side wall 88 of lower portion 44 of housing 40 and a side wall 90 of a canister 92 contained within lower portion 44. Lower portion 44 of housing 40 is substantially cylindrical, and includes a bottom wall 94 from which upstanding side wall 88 extends. Likewise, canister 92 is substantially cylindrical, and includes a bottom wall 96 adjacent the lower end of side wall 90. Spacer portions 98 extend below bottom wall 96 to support canister 92 so that bottom wall 96 is spaced above housing bottom wall 94. In this manner, water flows downwardly through flow path 86 and then past spacer portions 98 and into the gap formed between bottom wall 94 and canister bottom wall 96.

Canister bottom wall 96 is provided with a series of openings, shown at 100. Water flows upwardly through openings 100 and into the interior of canister 92, to mix with the water soluble chemical treatment, shown at 102, contained therein. The water circulates through the interior of canister 92 and mixes with chemical treatment 102 prior to exiting the interior of canister 92 through a dip tube 104. Dip tube 104 extends downwardly into the interior of canister 92 and includes a lower opening 106 for receiving mixed water and chemical treatment from the interior of canister 92. Mixed water and chemical treatment passes upwardly through dip tube 104 and through a downwardly extending nipple 108 provided on housing upper portion 42. Nipple 108 is in fluid communication with a passage 110 formed in the upper end of housing upper portion 42, from which mixed water and chemical treatment passes through outlet opening 50. As above described, the mixed water and chemical treatment then reenters cooling water system 10 through the various fluid lines above described.

With the above described construction, lower portion 44 of housing 40 is removable, thereby allowing access to its interior. This allows periodic replacement of canister 92 when chemical treatment 102 contained therein is completely dispensed into water circulating through housing 40. This design of housing 40 allows easy removal of lower portion 44 so as to provide quick interchangeability for replacing canister 92. To replace canister 92, an operator simply turns ring 46 a sufficient amount to release lower portion 44 from its connection thereto, and withdraws the empty canister 92. A full canister 92 is then inserted into lower portion 44. The upper end of dip tube 104 is aligned with nipple 108 so as to ensure an adequate seal between the incoming and outgoing water, and ring 46 is tightened so as to provide a secure connection of lower portion 44 to upper portion 42.

Dispensing apparatus 20 includes a safety pressure relief mechanism for ensuring that, prior to removal of lower portion 44 from upper portion 42, any fluid pressure within housing 40 is relieved. With reference to FIGS. 2 and 3, control box 78 is provided with a primary pressure relief switch 112. Switch 112 is interconnected with a dump valve 114, which is open to ambient pressure. Switch 112 is operable to actuate dump valve 114. Upon actuation of dump valve 114, fluid is drained from housing 40 through line 56 and dump valve 114 to relieve pressure in housing 40 prior to gaining access to its interior for changing canister 92. Because dip tube 104 extends downwardly into the interior of canister 92, the actuation of dump valve 114 creates a siphon effect within canister 92 so that fluid is drained from housing 40 to an elevation approximately equal to the elevation of dip tube opening 106. This ensures operator safety during changing of canisters by both relieving pressure within housing 40, which could otherwise cause burns due to the high temperature of liquid within housing 40, as well as draining a majority of the fluid within housing 40 therefrom prior to removal of lower portion 44.

Figures 5, 6:
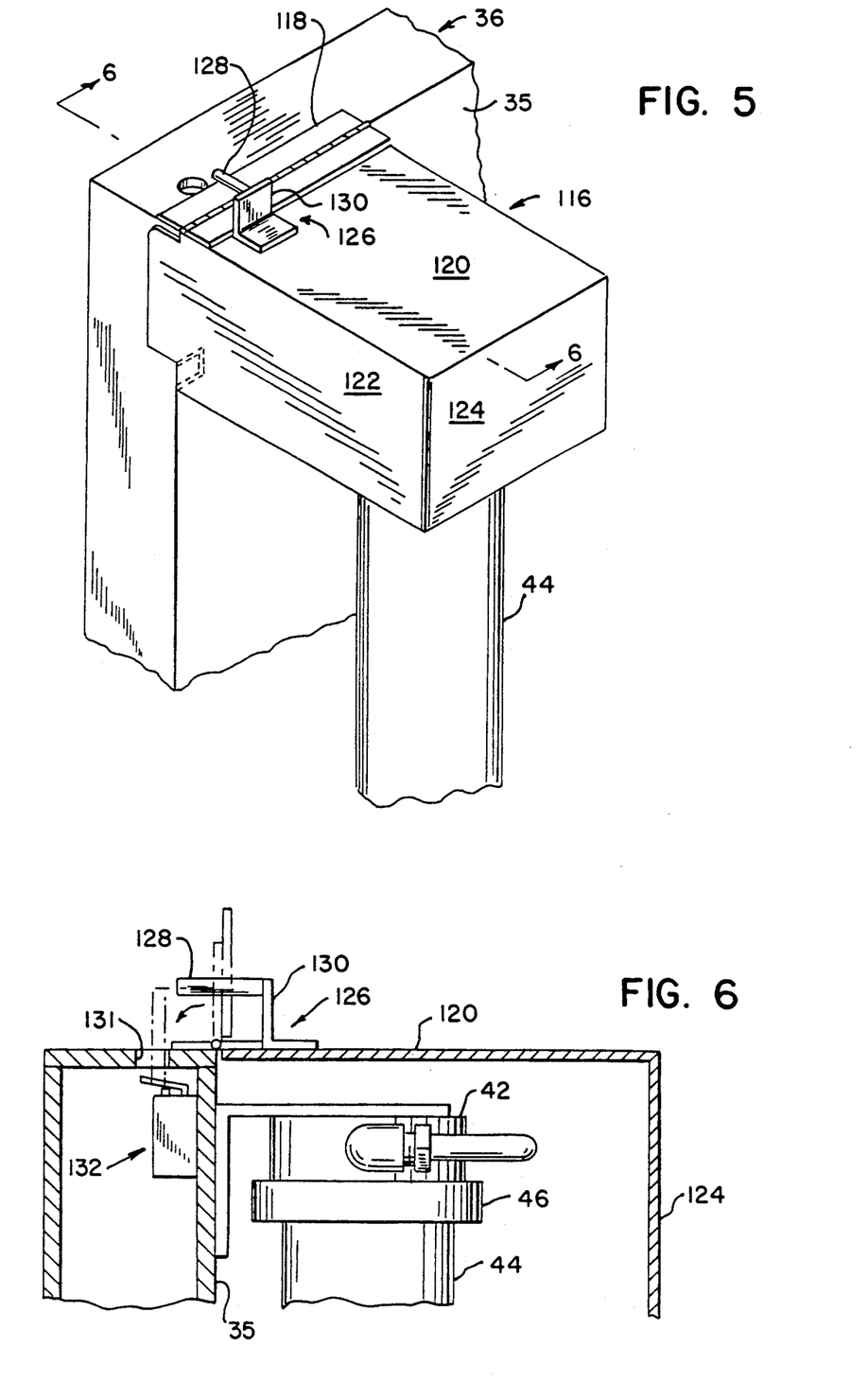
FIG. 5 is an isometric view showing the cover for preventing access to the housing interior.
FIG. 6 is a sectional view taken generally along line 6—6 of FIG. 5.

In the event the operator neglects to actuate dump valve 114 by switch 112 prior to changing canisters in housing 40, a safety back-up mechanism, shown in FIGS. 5 and 6, is employed to ensure that dump valve 114 is actuated. A cover, shown generally at 116, is pivotably connected to panel 36 by a hinge 118. Cover 116 includes a top wall 120, a side wall 122 and a front wall 124. Top wall 120 has a bracket 126 connected thereto, and an actuator 128 is connected to an upstanding leg 130 of bracket 126.

When cover 116 is in the position shown in FIG. 5, an operator cannot gain access to ring 46 so as to remove lower portion 44 of housing 40 from upper portion 42. Thus, canister 92 cannot be changed when cover 116 is in this position. In order to gain access to ring 46, cover 116 must be pivoted upwardly so as to expose ring 46. During the upward pivoting of cover 116, actuator 128 moves through an opening 131 and actuates a back-up switch 132 mounted on the backside of plate 35 of panel 36. Switch 132 is interconnected with dump valve 114, so as to actuate dump valve 114 prior to removal of lower portion 44 of housing 40 from upper portion 42. This construction ensures that an operator cannot gain access to the interior of housing 40 without first relieving pressure within housing 40 and draining at least a portion of the fluid from its interior. It should be understood that any satisfactory switching means, such as a magnetic switch or the like, may be used to achieve the same result as the switching mechanism described.

Control box 78 also includes an LED indicating light 134 and a reset button 136. As will be explained, the circuitry of the invention provides a predetermined time within which, when dispensing system 20 is actuated, the level of concentration of treatment chemicals within the water must rise to or above the predetermined optimal level of concentration. If the level of concentration does not rise to the optimal level within the predetermined time, dispensing apparatus 20 is shut down and LED indicator 134 is energized so as to indicate that canister 92 is empty. After changing canister 92 following the above-described steps, reset button 136 must be activated to reset the system and allow its subsequent operation.

Figure 7:
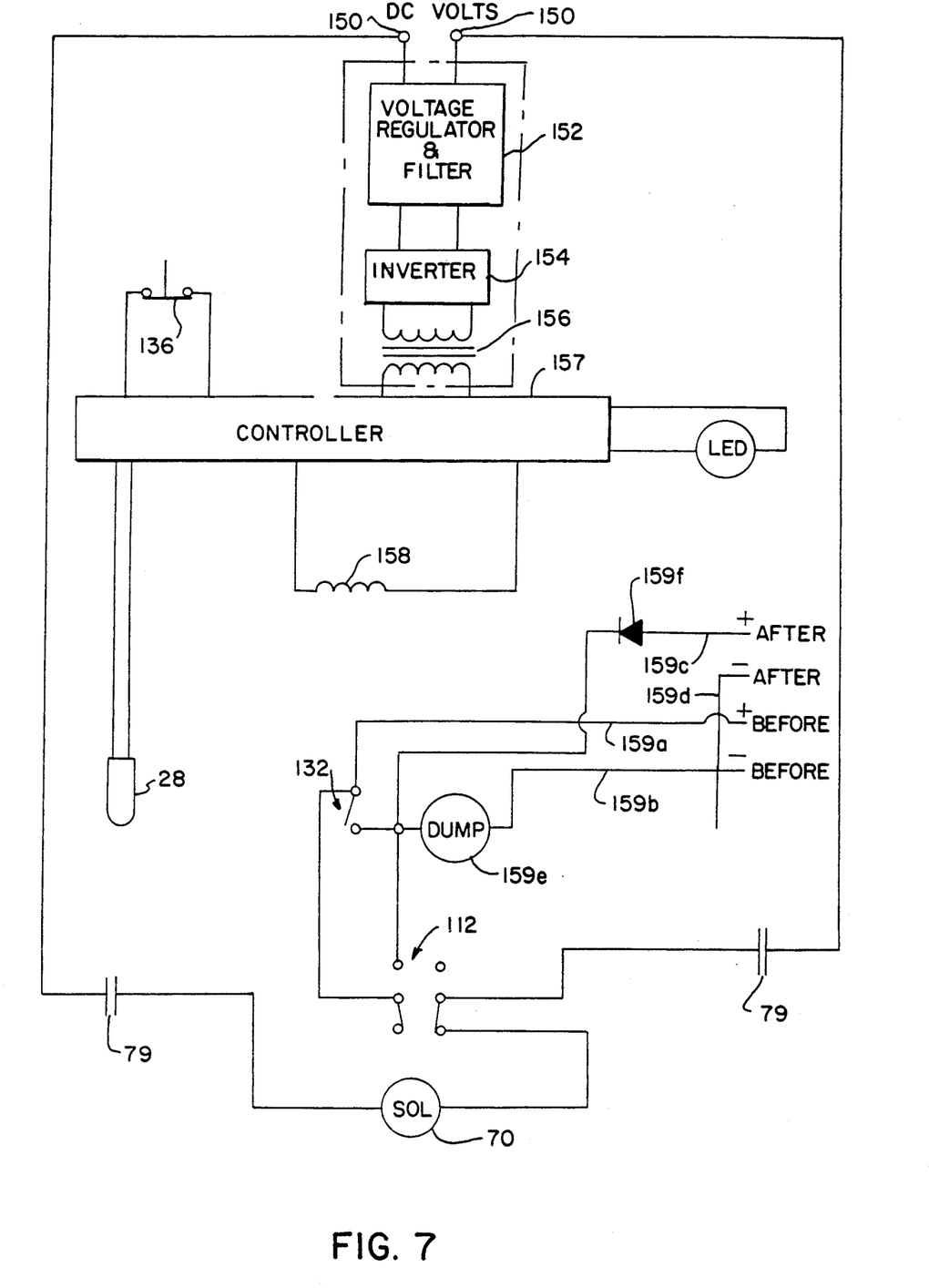
FIG. 7 is a block diagram of the electrical circuitry of the invention.

Turning now to FIG. 7, a block diagram of the novel electrical circuit incorporated in the water treatment dispensing system of the present invention is shown therein. The electrical circuit is connected at terminals 150 to the D.C. power system of the locomotive. Terminals 150 provide D.C. power to a filter and voltage regulator circuit 152 that removes voltage transients and other electrical noise from the power and provides a regulated D.C. voltage output. Such transients and noise tend to be of considerable size in a diesel-electric locomotive. Circuit 152 also regulates the output of the circuit to a constant D.C. voltage level.

Circuit 152 is connected to inverter 154 that inverts the D.C. voltage input to an A.C. voltage output and alters the A.C. voltage to a desired magnitude and frequency. The A.C. voltage output provided by inverter 154 permits the use of isolation transformer 156 connected in the output of the inverter. Isolation transformer 156 isolates the remaining portions of the electrical circuit from the power supply of the locomotive to insure that transients or other aberrations cannot affect the operation of the remaining portions.

The output of isolation transformer 156 is connected to conductivity control circuit 157. Conductivity control circuit 157 is connected to probe 28 and to relay coil 158 to operate relay contacts 79 responsive to the chemical condition of the locomotive engine coolant, as sensed by the probe. Relay contacts 79 and coil 158 control air solenoid valve 70 that, in turn, operates valves 34 and 60 to obtain the dispensing of the treatment chemical from canister housing 40 into the coolant.

As is known, the locomotive cooling system is provided with a temperature sensitive mechanism for draining coolant from the system at a predetermined low temperature to prevent freezing of the coolant in the system. The draining mechanism includes a temperature sensitive electrical switch. Buses 159a, 159b are interconnected with the locomotive circuitry before the temperature sensitive switch, and buses 159c, 159d are interconnected after the temperature sensitive switch. When the locomotive dump valve is actuated, a dump valve 159e is actuated by power from buses 159c, 159d to drain the dispensing system. Dump valve 159e is also actuable in response to switch 112 to drain the dispensing system for the purpose of changing dispensing canisters. A diode 159f blocks voltage returning on bus 159c to the locomotive dump valve. As previously mentioned, back-up switch 132 also acts to drain the dispensing system if manual switch 112 is not actuated.

Figure 8:
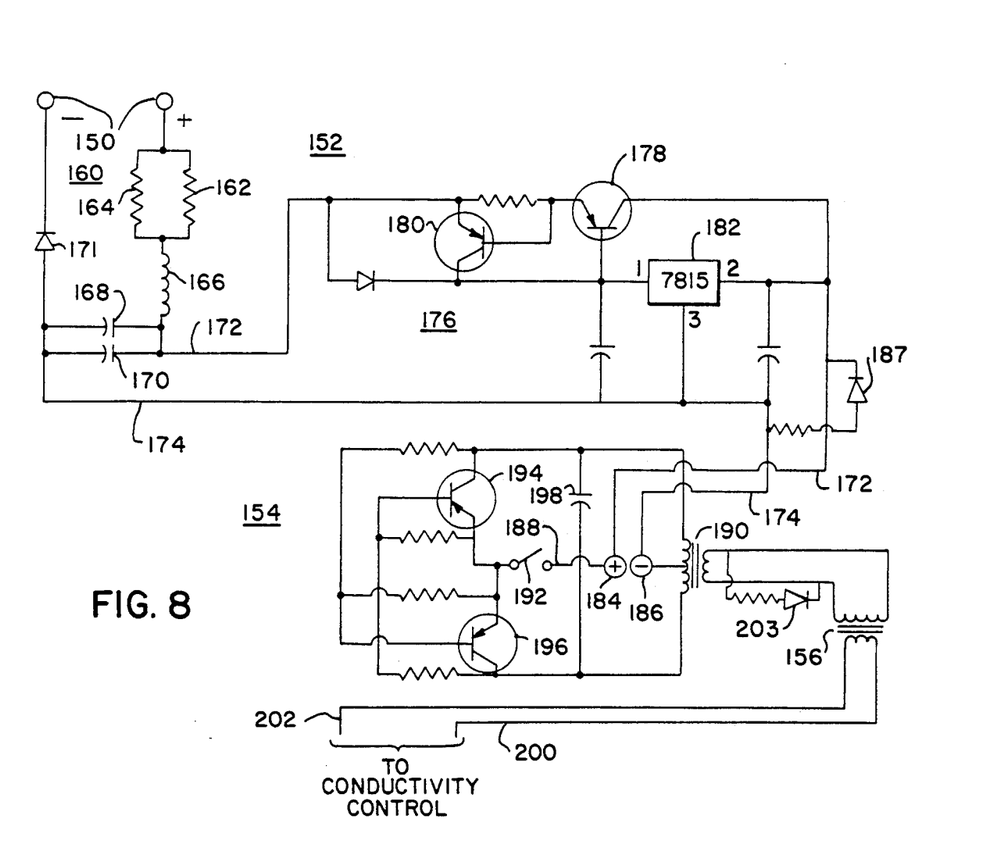
FIG. 8 is a diagram of the power supply and inverter circuits for supplying power to the dispensing apparatus from the locomotive electrical system.

Voltage regulation and filter circuit 152 is shown in detail in FIG. 8. Terminals 150 typically receive 32 volts D.C. from the locomotive power supply. The voltage at terminals 150 is passed through a filter network 160 including resistive elements 162-164, inductive element 166, and capacitive elements 168-170. The filter network removes transient spikes and other electrical noise from the D.C. voltage applied to terminals 150. Diode 171 protects against reverse connection of terminals 150 to the locomotive power supply. The output of filter network 160 is provided to buses 172 and 174.

Voltage regulator 176 is connected to buses 172 and 174. Voltage regulator 176 includes transistor 178, the emitter-collector circuit of which is arranged in bus 172. The base of transistor 178 is connected to transistor 180 that senses the voltage in conductor 172. The base of transistor 178 is also connected to voltage regulator 182, providing a regulating source. Voltage regulator 182 may be that manufactured by Texas Instruments under the designation 7815, or any other satisfactory regulator. Transistor 180 and regulator 182 control the conductivity of the emitter-collector circuit of transistor 178 and thus regulate the output voltage of circuitry 152 at terminals 184-186 to the constant level established by voltage regulator 182. An indicator such as light emitting diode 187 provides an indication that power is appearing at the output of voltage regulation and filter circuit 152.

Terminals 184-186 of buses 172 and 174 form the D.C. input to inverter 154. Terminals 184, 186 are interposed in center tap conductor 188 of the center tapped primary winding of transformer 190. Conductor 188 also contains on-off switch 192 and is connected intermediate the emitter-collector circuits of switching transistors 194 and 196. The ends of the center tapped primary winding of transformer 190 are connected in a complementary manner to the bases of transistors 194 and 196 and through appropriate resistors to the emitter-collector circuits of the transistors. Capacitor 198 connected across transformer 190 and transistors 194 and 196 protects the transistors against voltage transients.

The secondary winding of transformer 190 is connected to isolation transformer 156, the output of which is provided to conductivity control circuit 157 in conductors 200 and 202. The output at transformers 190 or 156 is 24 volts. The electrical characteristics of inverter 154, including transistors 194 and 196, may be selected such that the A.C. output voltage in conductors 200-202 has a frequency of 60 Hz.

An indicator 203, such as a light emitting diode, is provided across the secondary winding of transformer 190 to indicate that inverter 154 is operating.

Figure 9:
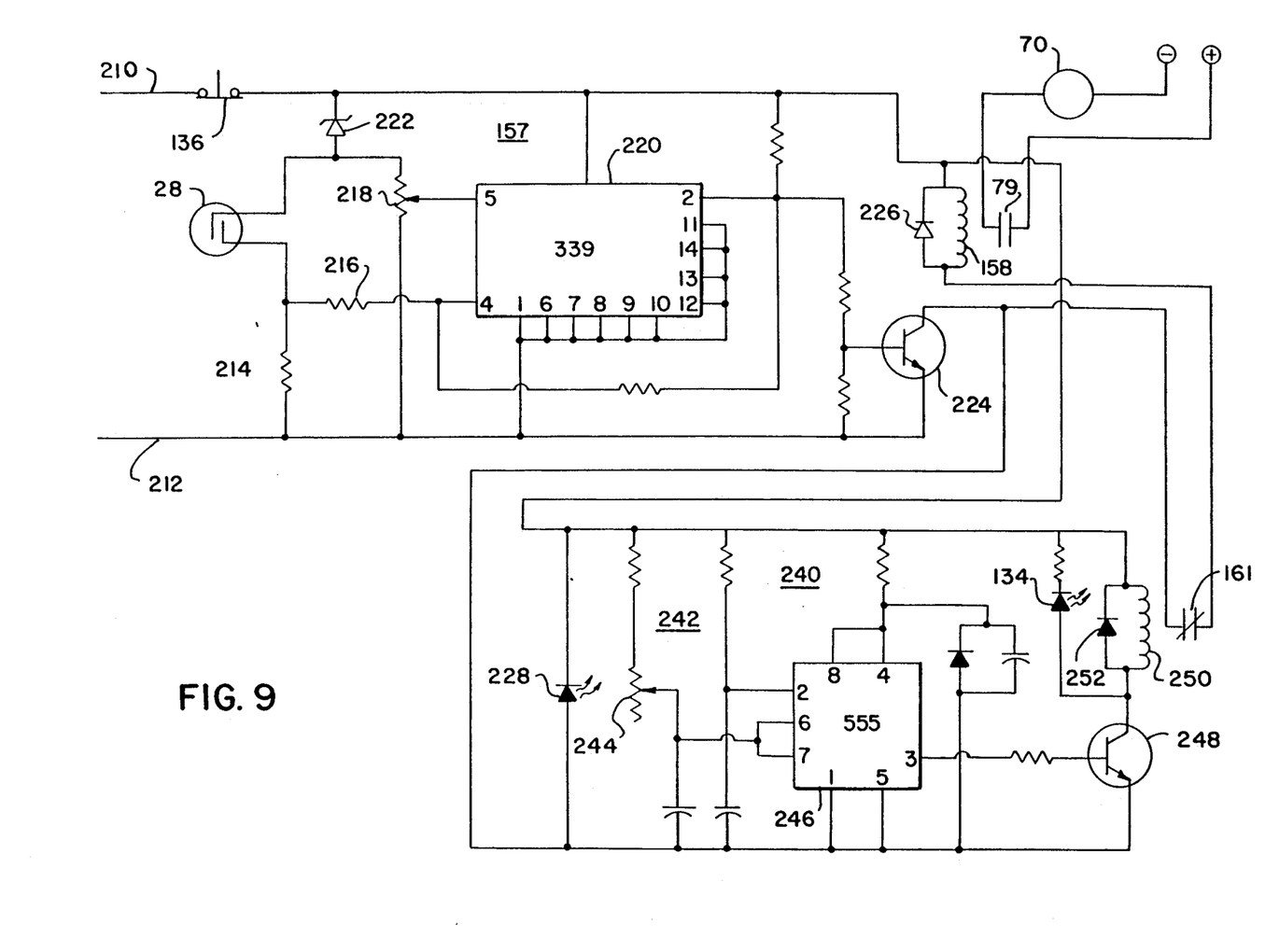
FIG. 9 is a circuit diagram of the conductivity control for the dispensing apparatus of FIG. 2.

The A.C. voltage in conductors 200-202 is provided to A.C. power buses 210 and 212 of conductivity control circuit 157, shown in detail in FIG. 9. Probe 28 is connected across A.C. power buses 210 and 212. The application of A.C. to probe 28 avoids the fouling of the probe that would otherwise eventually occur were D.C. used to energize the probe. Probe 28 is connected through resistor-potentiometer network 214, 216, 218 to the input of trigger circuit 220. Zener diode 222, connected to bus 210, is connected intermediate probe 28 and the resistive element of potentiometer 218. Trigger circuit 220 may be of the solid state type comprising the integrated circuit made and sold by Texas Instruments under the designation 339. Trigger circuit 220 is connected across buses 210-212 for being energized by the voltage in the buses.

Relay coil 158 and the emitter-collector circuit of transistor 224 are connected in series across buses 210-212 and in series with normally closed relay contacts 161. Diode 226 across relay coil 158 makes the current through the coil unidirectional. The base of transistor 224 is connected to the output of trigger circuit 220.

Probe 28 monitors the chemical condition of the coolant of the locomotive and provides an input signal to trigger circuit 220 proportional to the level of the treatment chemicals. The signal from probe 28 is compared with a preset constant established in trigger circuit 220. If the signal from probe 28 is greater than the preset constant, no output is provided from trigger circuit 220.

When the signal from probe 28 falls below the preset constant, an output signal is provided from trigger circuit 220 to the base of transistor 224. This renders the emitter-collector circuit of transistor 224 conductive, thus energizing relay coil 158, closing relay contacts 79, and commencing the dispensing of treatment chemical from canister housing 40.

When the signal from probe 28 again rises above the preset constant, the output signal from trigger circuit 220 is removed, rendering transistor 224 non-conductive, and deenergizing relay coil 158. This terminates the dispensing of treatment chemical from canister housing 40.

Indicator 228, such as an LED, is provided across A.C. buses 210-212 to provide an indication that conductivity control circuit 157 is receiving power. An indicator 228 is provided in parallel with relay coil 158 to provide unidirectional current flow and to indicate when the relay coil is energized and chemicals are being dispensed from canister housing 40.

As noted, supra, the circuitry of the present invention provides a predetermined time period within which, when dispensing system 20 is actuated, the level of concentration of treatment chemicals in the water must rise to or above the predetermined optimal level of concentration. If this does not occur, the dispensing apparatus is rendered inoperative and LED indicator 134 is energized to indicate that canister 92 is empty.

For this purpose, a timing circuit 240 is connected across power buses 210 and 212. Timing circuit 240 contains resistive-capacitor timing network 242. The timing interval of the network may be established by adjustable resistor 244. The output of the timing network is provided to a timing chip 246. Chip 246 may be of the solid state type comprising the integrated circuit made and sold by Texas Instruments under the designation 555. The output of circuit 246 is provided to the base of transistor 248. The emitter collector circuit of transistor 248 is connected in series with relay coil 250 having a diode 252 connected in parallel therewith. Relay coil 250 operates normally closed relay contacts 161 connected in series with transistor 224 and relay coil 158.

In the event control circuit 157 does not complete its operating cycle within the timing interval of timing network 242, timing chip 246 renders transistor 248 conductive. This energizes relay coil 250, opening relay contacts 161 and deenergizing relay coil 158 and moving solenoid 70 to a valve-closed condition. LED 134 provides an indication that the dispensing apparatus has been rendered inoperative due to failure to attain the desired concentration of chemical treatment within a time determined by timing chip 246. This permits the replacement of canister housing 40 containing the treatment chemical. The circuitry is reset by opening normally closed reset switch 136 in conductor 210.

Various alternatives and modifications are contemplated as being within the scope of the following claims particularly pointing out and distinctly claiming the invention.

We claim:

1. A vehicle, comprising:
   an engine having a cooling system circulating a coolant; and
   an apparatus for maintaining a predetermined level of concentration of chemicals in the coolant, comprising:
   sensing means for monitoring the level of concentration of chemicals in the coolant;
   flow through chemical dispensing means interconnected with said cooling system; and
   flow control means responsive to said sensing means for preventing the flow of coolant through said dispensing means when the level of concentration of chemicals is at or above said predetermined level, and for allowing coolant to circulate through said dispensing means and back into said cooling system when the level of concentration of chemicals in said system falls below said predetermined level, so as to raise the level of concentration of chemicals in said system to said predetermined level, whereafter said flow control means discontinues circulation of coolant through said dispensing means in response to detection of said predetermined level of concentration of chemicals by said sensing means.

2. The vehicle of claim 1, wherein said sensing means comprises a probe disposed within said cooling system for measuring the conductivity of coolant within said system and thereby the level of concentration of chemicals in the coolant, and a comparator for ascertaining whether, based on the conductivity reading of the coolant, the level of concentration of chemicals in the coolant is at or above said predetermined level.

3. The vehicle of claim 1, wherein said chemical dispensing means comprises a housing for holding a quantity of soluble chemical fluid treatment in its interior, and wherein said coolant is introduced into said housing through an inlet line connected between said circulating system and said housing and circulates through the interior of said housing for mixing with said chemical treatment prior to circulation between said housing and said system, so as to raise the level of chemical concentration of coolant in said system during fluid flow through said housing.

4. The vehicle of claim 3, wherein said housing is adapted to house in its interior a canister containing a predetermined quantity of chemical treatment, said canister being adapted to accommodate flow of coolant through said housing and allowing said coolant to mix with said chemical concentrate during passage through said housing.

5. A vehicle, comprising:
   an engine having a cooling system circulating a coolant and generating D.C. electrical power;
   an apparatus for maintaining a predetermined level of concentration of chemicals in the coolant, comprising:
   sensing means for monitoring the level of concentration of chemicals in the coolant;
   flow control means comprising electrically operable fluid controlling valve means responsive to said sensing means for preventing the flow of coolant through said dispensing means when the level of concentration of chemicals is at or above said predetermined level, and for allowing coolant from said cooling system to circulate through said dispensing means and back into said cooling system when the level of concentration of chemicals in said coolant falls below said predetermined level, so as to raise the level of concentration of chemicals in said coolant to said predetermined level, whereafter said valve means discontinues circulation of coolant through said dispensing means in response to detection of said predetermined level of concentration of chemicals by said sensing means; and
   actuator means including circuitry interposed between said sensing means and said valve means for operating said valve means, wherein said circuitry provides A.C. energization to said actuator means from the D.C. electrical power generated by said engine.

6. The vehicle of claim 5, wherein said sensing means is further defined as one for sensing conductivity of the circulating coolant 7. The vehicle of claim 5, wherein said flow control means includes timing means disabling said apparatus in the event the concentration of chemicals in the coolant is not raised to said predetermined level within a predetermined time.

8. The vehicle of claim 5, wherein said flow control means includes indicators indicating whether coolant is flowing through said chemical dispensing means.

9. The vehicle of claim 5, wherein said actuator means further includes means for isolating said circuitry from alterations in said D.C. electrical power generated by said engine.

10. The vehicle of claim 9, wherein said isolating means comprises voltage regulation and filtering means.

11. The vehicle of claim 5, wherein said sensing means is further defined as one for sensing the conductivity of the circulating coolant and wherein said actuator means includes means for obtaining A.C. from said D.C. electrical power generated by said engine for providing A.C. energization to said sensing means.

12. The vehicle of claim 11, wherein said A.C. providing means includes an inverter.

13. The vehicle of claim 12, wherein said actuator means includes an isolating transformer coupled to the output of said inverter.

* * * * *